（12） United States Patent
Beyar et al.

(10) Patent No.: US 9,526,549 B2
(45) Date of Patent: Dec. 27, 2016

(54) BONE SCREW WITH INSERT

(71) Applicant: Carbofix Orthopedics Ltd., Herzlia Pituach (IL)

(72) Inventors: Mordechay Beyar, Caesarea (IL); Oren Globerman, Kfar-Shemaryahu (IL)

(73) Assignee: Carbofix Orthopedics Ltd., Herzlia Pituach (IL)

( * ) Notice: Subject to any disclaimer, the term of this patent is extended or adjusted under 35 U.S.C. 154(b) by 522 days.

(21) Appl. No.: 13/852,100

(22) Filed: Mar. 28, 2013

(65) Prior Publication Data

US 2013/0237813 A1  Sep. 12, 2013

Related U.S. Application Data

(63) Continuation-in-part of application No. 13/742,462, filed on Jan. 16, 2013.

(60) Provisional application No. 61/617,067, filed on Mar. 29, 2012, provisional application No. 61/641,900, filed on May 3, 2012, provisional application No. 61/586,853, filed on Jan. 16, 2012, provisional application No. 61/617,067, filed on Mar. 29, 2012, provisional application No. 61/641,900, filed on May 3, 2012.

(51) Int. Cl.
*A61B 17/86* (2006.01)
*A61B 6/12* (2006.01)
*A61B 6/00* (2006.01)
*B29D 1/00* (2006.01)

(52) U.S. Cl.
CPC ............. *A61B 17/8685* (2013.01); *A61B 6/12* (2013.01); *A61B 6/485* (2013.01); *A61B 17/866* (2013.01); *A61B 17/8635* (2013.01); *B29D 1/00* (2013.01); *A61B 2090/3966* (2016.02)

(58) Field of Classification Search
CPC ............ A61B 17/8625; A61B 17/8685; A61B 17/8052; A61B 17/1728
USPC .................. 606/300–331; 411/383, 396, 413
See application file for complete search history.

(56) References Cited

U.S. PATENT DOCUMENTS

| | | |
|---|---|---|
| 3,630,253 A | 12/1971 | Sherman |
| 4,058,581 A | 11/1977 | Park |
| 4,220,187 A | 9/1980 | Holmes |
| 4,667,664 A | 5/1987 | Taylor et al. |
| 4,706,659 A | 11/1987 | Matthews et al. |
| 4,718,801 A | 1/1988 | Berecz |
| 4,750,905 A | 6/1988 | Koeneman et al. |
| 4,824,314 A | 4/1989 | Stencel |
| 4,863,330 A | 9/1989 | Olez et al. |

(Continued)

FOREIGN PATENT DOCUMENTS

| | | |
|---|---|---|
| CN | 1170380 | 1/1998 |
| CN | 1324278 | 11/2001 |

(Continued)

OTHER PUBLICATIONS

Decision of Rejection Dated Mar. 3, 2015 From the Japanese Patent Office Re. Application No. 2011-545832 and Its Translation Into English.

(Continued)

*Primary Examiner* — Christopher Beccia

(57) ABSTRACT

A composite material bone screw comprising an embedded insert. The embedded insert may serve as a thread cutting tool by covering at least one cutting edge of the screw.

21 Claims, 11 Drawing Sheets

(56) References Cited

U.S. PATENT DOCUMENTS

| | | | |
|---|---|---|---|
| 4,875,474 A | 10/1989 | Border | |
| 4,978,360 A | 12/1990 | Devanathan | |
| 4,988,350 A | 1/1991 | Herzberg | |
| 5,009,664 A | 4/1991 | Sievers | |
| 5,032,125 A | 7/1991 | Durham et al. | |
| 5,041,113 A | 8/1991 | Biedermann et al. | |
| 5,060,635 A | 10/1991 | Steur et al. | |
| 5,064,439 A | 11/1991 | Chang et al. | |
| 5,181,930 A | 1/1993 | Dumbleton et al. | |
| 5,192,330 A | 3/1993 | Chang et al. | |
| 5,197,966 A | 3/1993 | Sommerkamp | |
| 5,292,215 A | 3/1994 | Roberts, III | |
| 5,397,358 A | 3/1995 | Wenner et al. | |
| 5,498,265 A | 3/1996 | Asnis | |
| 5,522,817 A | 6/1996 | Sander et al. | |
| 5,795,116 A | 8/1998 | Frank et al. | |
| 5,824,079 A | 10/1998 | Siegler et al. | |
| 5,879,352 A | 3/1999 | Filoso et al. | |
| 5,961,524 A | 10/1999 | Crombie | |
| 6,030,389 A | 2/2000 | Wagner et al. | |
| 6,206,881 B1 | 3/2001 | Frigg et al. | |
| 6,342,055 B1 | 1/2002 | Eisermann et al. | |
| 6,471,707 B1 | 10/2002 | Miller et al. | |
| 6,605,090 B1 | 8/2003 | Trieu et al. | |
| 6,692,497 B1 | 2/2004 | Tormala et al. | |
| 6,692,498 B1 | 2/2004 | Niiranen et al. | |
| 6,730,091 B1 | 5/2004 | Pfefferle et al. | |
| 6,916,321 B2* | 7/2005 | TenHuisen | A61B 17/8685 606/312 |
| 6,921,402 B2 | 7/2005 | Contiliano et al. | |
| 7,419,714 B1 | 9/2008 | Magerl et al. | |
| 7,785,325 B1 | 8/2010 | Milbank | |
| 7,896,599 B2 | 3/2011 | Stephen et al. | |
| 7,914,244 B2 | 3/2011 | Bubulka et al. | |
| 8,128,627 B2 | 3/2012 | Justin et al. | |
| 8,323,321 B2 | 12/2012 | Gradl | |
| 8,709,055 B2 | 4/2014 | Beyar et al. | |
| 2002/0029043 A1 | 3/2002 | Ahrens et al. | |
| 2002/0133172 A1 | 9/2002 | Lambrecht et al. | |
| 2002/0156473 A1 | 10/2002 | Bramlet et al. | |
| 2003/0057590 A1 | 3/2003 | Loher et al. | |
| 2003/0158555 A1 | 8/2003 | Sanders et al. | |
| 2004/0073218 A1 | 4/2004 | Dahners | |
| 2004/0260291 A1 | 12/2004 | Jensen | |
| 2005/0096656 A1 | 5/2005 | Behrens | |
| 2005/0131413 A1 | 6/2005 | O'Driscoll et al. | |
| 2005/0177153 A1 | 8/2005 | Guzman et al. | |
| 2005/0192578 A1 | 9/2005 | Horst | |
| 2005/0234457 A1 | 10/2005 | James et al. | |
| 2006/0004431 A1 | 1/2006 | Fuller et al. | |
| 2006/0009771 A1 | 1/2006 | Orbay et al. | |
| 2006/0015110 A1 | 1/2006 | Pepper | |
| 2006/0041261 A1* | 2/2006 | Osypka | A61B 17/8685 606/308 |
| 2006/0079900 A1 | 4/2006 | Mathieu et al. | |
| 2006/0116678 A1 | 6/2006 | Impellizzeri | |
| 2006/0189996 A1 | 8/2006 | Orbay et al. | |
| 2006/0195085 A1 | 8/2006 | Happonen et al. | |
| 2006/0200142 A1 | 9/2006 | Sohngen et al. | |
| 2006/0235400 A1 | 10/2006 | Schneider | |
| 2006/0259039 A1 | 11/2006 | Pitkanen et al. | |
| 2006/0264948 A1 | 11/2006 | Williams | |
| 2006/0282168 A1 | 12/2006 | Sherman et al. | |
| 2007/0083207 A1 | 4/2007 | Ziolo et al. | |
| 2007/0110544 A1 | 5/2007 | Friederich et al. | |
| 2007/0123878 A1 | 5/2007 | Shaver | |
| 2007/0162018 A1 | 7/2007 | Jensen et al. | |
| 2007/0167953 A1 | 7/2007 | Prien et al. | |
| 2007/0173843 A1 | 7/2007 | Matityahu | |
| 2007/0233105 A1 | 10/2007 | Nelson et al. | |
| 2007/0260244 A1 | 11/2007 | Wolter | |
| 2008/0046091 A1 | 2/2008 | Weiss et al. | |
| 2008/0140130 A1 | 6/2008 | Chan et al. | |
| 2008/0195157 A1 | 8/2008 | Orschler et al. | |
| 2008/0208259 A1 | 8/2008 | Gilbert et al. | |
| 2008/0234752 A1 | 9/2008 | Dahners | |
| 2008/0234762 A1* | 9/2008 | Forstein | A61B 17/8635 606/312 |
| 2008/0287951 A1 | 11/2008 | Stoneburner et al. | |
| 2008/0294201 A1 | 11/2008 | Huddleston, III | |
| 2009/0018588 A1 | 1/2009 | Eckhof et al. | |
| 2009/0088807 A1 | 4/2009 | Castaneda et al. | |
| 2009/0228008 A1 | 9/2009 | Justin et al. | |
| 2009/0228048 A1 | 9/2009 | Duncan et al. | |
| 2009/0248089 A1* | 10/2009 | Jacofsky | A61B 17/686 606/311 |
| 2009/0312803 A1 | 12/2009 | Austin et al. | |
| 2010/0016858 A1 | 1/2010 | Michel | |
| 2010/0042215 A1 | 2/2010 | Stalcup et al. | |
| 2010/0094423 A1 | 4/2010 | Foley et al. | |
| 2010/0100134 A1 | 4/2010 | Mocanu | |
| 2010/0190138 A1* | 7/2010 | Giorno | A61C 8/0022 433/174 |
| 2010/0217333 A1* | 8/2010 | McShane | A61B 17/8883 606/305 |
| 2010/0234847 A1 | 9/2010 | Impellizzeri | |
| 2010/0312286 A1 | 12/2010 | Dell'Oca | |
| 2010/0331842 A1 | 12/2010 | Milbank | |
| 2011/0015682 A1 | 1/2011 | Lewis et al. | |
| 2011/0106086 A1 | 5/2011 | Laird | |
| 2011/0218570 A1 | 9/2011 | Felix et al. | |
| 2011/0224737 A1 | 9/2011 | Lewis et al. | |
| 2011/0282395 A1 | 11/2011 | Beyar et al. | |
| 2011/0288598 A1 | 11/2011 | Moed et al. | |
| 2011/0295319 A1* | 12/2011 | Duplessis | A61B 17/1655 606/264 |
| 2012/0059376 A1 | 3/2012 | Rains et al. | |
| 2012/0065638 A1 | 3/2012 | Moore | |
| 2012/0083847 A1 | 4/2012 | Huebner et al. | |
| 2012/0136396 A1 | 5/2012 | Baker et al. | |
| 2012/0203285 A1 | 8/2012 | Rotini et al. | |
| 2012/0283790 A1 | 11/2012 | Meyer, III | |
| 2012/0330361 A1* | 12/2012 | Gepstein | A61B 17/7023 606/254 |
| 2013/0079829 A1 | 3/2013 | Globerman et al. | |
| 2013/0116693 A1 | 5/2013 | Nelson et al. | |
| 2013/0184765 A1 | 7/2013 | Beyar et al. | |
| 2013/0218214 A1 | 8/2013 | Beyar et al. | |
| 2013/0261675 A1 | 10/2013 | Fritzinger | |
| 2013/0296863 A1 | 11/2013 | Globerman et al. | |
| 2013/0296952 A1 | 11/2013 | Globerman et al. | |
| 2013/0325007 A1 | 12/2013 | Beyar et al. | |
| 2014/0222001 A1 | 8/2014 | Beyar et al. | |
| 2015/0327893 A1 | 11/2015 | Beyar et al. | |
| 2016/0067046 A1 | 3/2016 | Globerman et al. | |
| 2016/0113695 A1 | 4/2016 | Globerman et al. | |

FOREIGN PATENT DOCUMENTS

| | | |
|---|---|---|
| CN | 1367669 | 9/2002 |
| CN | 1482890 | 3/2004 |
| CN | 1586416 | 3/2005 |
| CN | 2746884 | 12/2005 |
| CN | 1819799 | 8/2006 |
| CN | 101304695 | 11/2008 |
| DE | 4343117 | 6/1995 |
| EP | 1042989 | 10/2000 |
| EP | 1101459 | 5/2001 |
| EP | 1598028 | 11/2005 |
| EP | 1733704 | 12/2006 |
| EP | 1779796 | 5/2007 |
| EP | 1857066 | 11/2007 |
| EP | 2198792 | 6/2010 |
| EP | 2292176 | 3/2011 |
| FR | 2555902 | 6/1985 |
| FR | 2646767 | 11/1990 |
| FR | 2829378 | 3/2003 |
| GB | 2442706 | 4/2008 |
| JP | 02-198550 | 8/1990 |
| JP | 05-000157 | 1/1993 |
| JP | 05-092019 | 4/1993 |
| JP | 06-500945 | 2/1994 |
| JP | 2002-536048 | 10/2002 |

(56) References Cited

FOREIGN PATENT DOCUMENTS

| JP | 2007-125387 | 5/2007 |
|---|---|---|
| JP | 2008-036094 | 2/2008 |
| RU | 1111748 | 7/1984 |
| WO | WO 92/18068 | 10/1992 |
| WO | WO 93/13713 | 7/1993 |
| WO | WO 94/07425 | 4/1994 |
| WO | WO 96/02203 | 2/1996 |
| WO | WO 96/09014 | 3/1996 |
| WO | WO 96/19336 | 6/1996 |
| WO | WO 01/15637 | 3/2001 |
| WO | WO 2006/090226 | 8/2006 |
| WO | WO 2007/009123 | 1/2007 |
| WO | WO 2007/010671 | 1/2007 |
| WO | WO 2007/035772 | 3/2007 |
| WO | WO 2008/033742 | 3/2008 |
| WO | WO 2008/064346 | 5/2008 |
| WO | WO 2008/092192 | 8/2008 |
| WO | WO 2009/002890 | 12/2008 |
| WO | WO 2009/143374 | 11/2009 |
| WO | WO 2009/152270 | 12/2009 |
| WO | WO 2009/152272 | 12/2009 |
| WO | WO 2010/045473 | 4/2010 |
| WO | WO 2010/082183 | 7/2010 |
| WO | WO 2011/042407 | 4/2011 |
| WO | WO 2011/154891 | 12/2011 |
| WO | WO 2012/107913 | 8/2012 |

OTHER PUBLICATIONS

Official Action Dated Mar. 17, 2015 From the US Patent and Trademark Office Re. U.S. Appl. No. 13/702,334.
Office Action Dated Jan. 22, 2015 From the Israel Patent Office Re. Application No. 223485.
Official Action Dated Jan. 22, 2015 From the US Patent and Trademark Office Re. U.S. Appl. No. 14/246,161.
Translation Dated Feb. 9, 2015 of Office Action Dated Jan. 22, 2015 From the Israel Patent Office Re. Application No. 223485.
Official Action Dated Dec. 19, 2014 From the US Patent and Trademark Office Re. U.S. Appl. No. 13/742,462. (Part I).
Official Action Dated Dec. 19, 2014 From the US Patent and Trademark Office Re. U.S. Appl. No. 13/742,462. (Part II).
Official Action Dated Dec. 23, 2014 From the US Patent and Trademark Office Re. U.S. Appl. No. 13/935,501.
Official Action Dated Dec. 19, 2014 From the US Patent and Trademark Office Re. U.S. Appl. No. 13/935,497.
Official Action Dated Aug. 5, 2014 From the US Patent and Trademark Office Re. U.S. Appl. No. 13/935,497.
Official Action Dated Jul. 11, 2014 From the US Patent and Trademark Office Re. U.S. Appl. No. 13/935,501.
Official Action Dated Jul. 17, 2014 From the US Patent and Trademark Office Re. U.S. Appl. No. 14/246,161.
Applicant-Initiated Interview Summary Dated Oct. 17, 2013 From the US Patent and Trademark Office Re. U.S. Appl. No. 13/144,938.
Communication Pursuant to Article 94(3) EPC Dated Jul. 2, 2013 From the European Patent Office Re. Application No. 10702750.0.
Notice of Allowance Dated Apr. 2, 2015 From the US Patent and Trademark Office Re. U.S. Appl. No. 13/935,497.
Notice of Allowance Dated Apr. 3, 2015 From the US Patent and Trademark Office Re. U.S. Appl. No. 14/246,161.
Official Action Dated Apr. 1, 2015 From the US Patent and Trademark Office Re. U.S. Appl. No. 13/935,501.
Requisition by the Examiner and Examination Search Report Dated Mar. 17, 2015 From the Canadian Intellectual Property Office Re. Application No. 2,749,684.
Applicant-Initiated Interview Summary Dated Nov. 21, 2014 From the US Patent and Trademark Office Re. U.S. Appl. No. 13/935,497.
Communication Pursuant to Article 94(3) EPC Dated Nov. 19, 2014 From the European Patent Office Re. Application No. 10702750.0.
Restriction Official Action Dated May 30, 2014 From the US Patent and Trademark Office Re. U.S. Appl. No. 14/246,161.

Notification of Office Action Dated Mar. 7, 2014 From the State Intellectual Property Office of the People's Republic of China Re. Application No. 201080012276.1 and Its Translation Into English.
Advisory Action Before the Filing of an Appeal Brief Dated Jun. 29, 2015 From the US Patent and Trademark Office Re. U.S. Appl. No. 13/702,334.
Official Action Dated Jun. 12, 2015 From the US Patent and Trademark Office Re. U.S. Appl. No. 13/742,462.
Notification of Office Action Dated Oct. 29, 2014 From the State Intellectual Property Office of the People's Republic of China Re. Application No. 201180038951.2 and Its Translation Into English.
Search Report Dated Oct. 29, 2014 From the State Intellectual Property Office of the People's Republic of China Re. Application No. 201180038951.2 and Its Translation Into English.
Translation of Notification of Office Action Dated Apr. 12, 2013 From the State Intellectual Property Office of the People's Republic of China Re. Application No. 201080012276.1.
Translation of Search Report Dated Apr. 12, 2013 From the State Intellectual Property Office of the People's Republic of China Re. Application No. 201080012276.1.
European Search Report and the Written Opinion Dated Apr. 18, 2013 From the European Patent Office Re. Application No. 13151490.3.
Restriction Official Action Dated Mar. 22, 2013 From the US Patent and Trademark Office Re. U.S. Appl. No. 13/144,938.
Communication Relating to the Results of the Partial International Search Dated May 17, 2010 From the International Searching Authority Re.: Application No. PCT/IB2010/050225.
Communication Relating to the Results of the Partial International Search Dated May 29, 2012 From the International Searching Authority Re. Application No. PCT/IB2012/050645.
Communication Relating to the Results of the Partial International Search Dated Sep. 29, 2011 From the International Searching Authority Re. Application No. PCT/IB2011/052468.
International Preliminary Report on Patentability Dated Dec. 20, 2012 From the International Bureau of WIPO Re. Application No. PCT/IB2011/052468.
International Preliminary Report on Patentability Dated Jul. 28, 2011 From the International Bureau of WIPO Re. Application No. PCT/IB2010/050225.
International Search Report and the Written Opinion Dated Nov. 10, 2010 From the International Searching Authority Re: Application No. PCT/IB2010/050225.
International Search Report and the Written Opinion Dated Aug. 24, 2012 From the International Searching Authority Re: Application No. PCT/IB2010/050225.
International Search Report and the Written Opinion Dated Dec. 29, 2011 From the International Searching Authority Re. Application No. PCT/IB2011/052468.
Applicant-Initiated Interview Summary Dated Oct. 8, 2014 From the US Patent and Trademark Office Re. U.S. Appl. No. 13/935,501.
Office Action Dated Aug. 10, 2014 From the Israel Patent Office Re. Application No. 214105 and Its Translation Into English.
Communication Pursuant to Article 94(30 EPC Dated Jul. 11, 2014 From the European Patent Office Re. Application No. 13151490.3.
Restriction Official Action Dated Aug. 1, 2014 From the US Patent and Tradmark Office Re. U.S. Appl. No. 13/742,462.
Office Action Dated Apr. 2, 2014 From the Israel Patent Office Re. Application No. 214105 and Its Translation Into English.
Corrected Notice of Allowability Dated Feb. 11, 2014 From the US Patent and Trademark Office Re. U.S. Appl. No. 13/144,938.
Official Action Dated Jan. 27, 2014 From the US Patent and Trademark Office Re. U.S. Appl. No. 13/935,501.
Notice of Allowance Dated Dec. 11, 2013 From the US Patent and Trademark Office Re. U.S. Appl. No. 13/144,938.
Notification of Office Action Dated Oct. 18, 2013 From the State Intellectual Property Office of the People's Republic of China Re. Application No. 201080012276.1 and Its Translation Into English.
Translation of Search Report Dated Oct. 18, 2013 From the State Intellectual Property Office of the People's Republic of China Re. Application No. 201080012276.1.

(56) References Cited

OTHER PUBLICATIONS

International Preliminary Report on Patentability Dated Aug. 22, 2013 From the International Bureau of WIPO Re. Application No. PCT/IB2012/050645.
Notice of Reason for Rejection Dated Jun. 3, 2014 From the Japanese Patent Office Re. Application No. 2011-545832 and Its Translation Into English.
Corrected Notice of Allowability Dated Feb. 14, 2014 From the US Patent and Trademark Office Re. U.S. Appl. No. 13/144,938.
Notice of Reason for Rejection Dated Nov. 15, 2013 From the Japanese Patent Office Re. Application No. 2011-545832 and Its Translation Into English.
Communication Pursuant to Rules 70(2) and 70a(2) EPC and Reference to Rule 39(1) EPC Dated Jul. 22, 2013 From the European Patent Office Re. Application No. 13151490.3.
Official Action Dated Jun. 27, 2013 From the US Patent and Trademark Office Re. U.S. Appl. No. 13/144,938.
Official Action Dated Apr. 29, 2015 From the US Patent and Trademark Office Re. U.S. Appl. No. 13/985,048.
Communication Pursuant to Article 94(3) EPC Dated Apr. 29, 2015 From the European Patent Office Re. Application No. 13151490.3.
Applicant-Initiated Interview Summary Dated Jun. 9, 2015 From the US Patent and Trademark Office Re. U.S. Appl. No. 13/702,334.
Official Action Dated Nov. 10, 2014 From the US Patent and Trademark Office Re. U.S. Appl. No. 13/702,334.
Applicant-Initiated Interview Summary Dated Oct. 19, 2015 From the US Patent and Trademark Office Re. U.S. Appl. No. 13,742,462.
Translation Dated Dec. 20, 2015 of Notification of Office Action and Search Report Dated Dec. 20, 2015 From the State Intellectual Property Office of the People's Republic of China Re. Application No. 201410413164.7.
Applicant-Initiated Interview Summary, Dated Dec. 22, 2015 From the US Patent and Trademark Office Re. U.S. Appl. No. 13/702,334.
Notification of Office Action Dated Dec. 28, 2015 From the State Intellectual Property Office of the People's Republic of China Re. Application No. 201410413073.3.
Notification of Office Action and Search Report Dated Jan. 13, 2016 From the State Intellectual Property Office of the People's Republic of China Re. Application No. 201410412613.6.
Translation Dated Jan. 17, 2016 of Notification of Office Action Dated Dec. 28, 2015 From the State Intellectual Property Office of the People's Republic of China Re. Application No. 201410413073.3.
Translation Dated Jan. 27, 2016 of Notification of Office Action Dated Jan. 13, 2016 From the State Intellectual Property Office of the People's Republic of China Re. Application No. 201410412613.6.
Notification of Office Action and Search Report Dated Dec. 2, 2015 From the State Intellectual Property Office of the People's Republic of China Re. Application No. 201410413164.7.
Communication Pursuant to Article 94(3) EPC Dated Feb. 2, 2016 From the European Patent Office Re. Application No. 13151490.3.
Official Action Dated Feb. 1, 2016 From the US Patent and Trademark Office Re. Application No. 13/852,145.
Official Action Dated Jan. 29, 2016 From the US Patent and Trademark Office Re. U.S. Appl. No. 13/985,048.
Advisory Action Before the Filing of an Appeal Brief Dated May 9, 2016 From the US Patent and Trademark Office Re. U.S. Appl. No. 13/985,048.
Official Action Dated Mar. 17, 2016 From the US Patent and Trademark Office Re. U.S. Appl. No. 13/742,462.
Official Action Dated Aug. 21, 2015 From the US Patent and Trademark Office Re. U.S. Appl. No. 13/702,334.

* cited by examiner

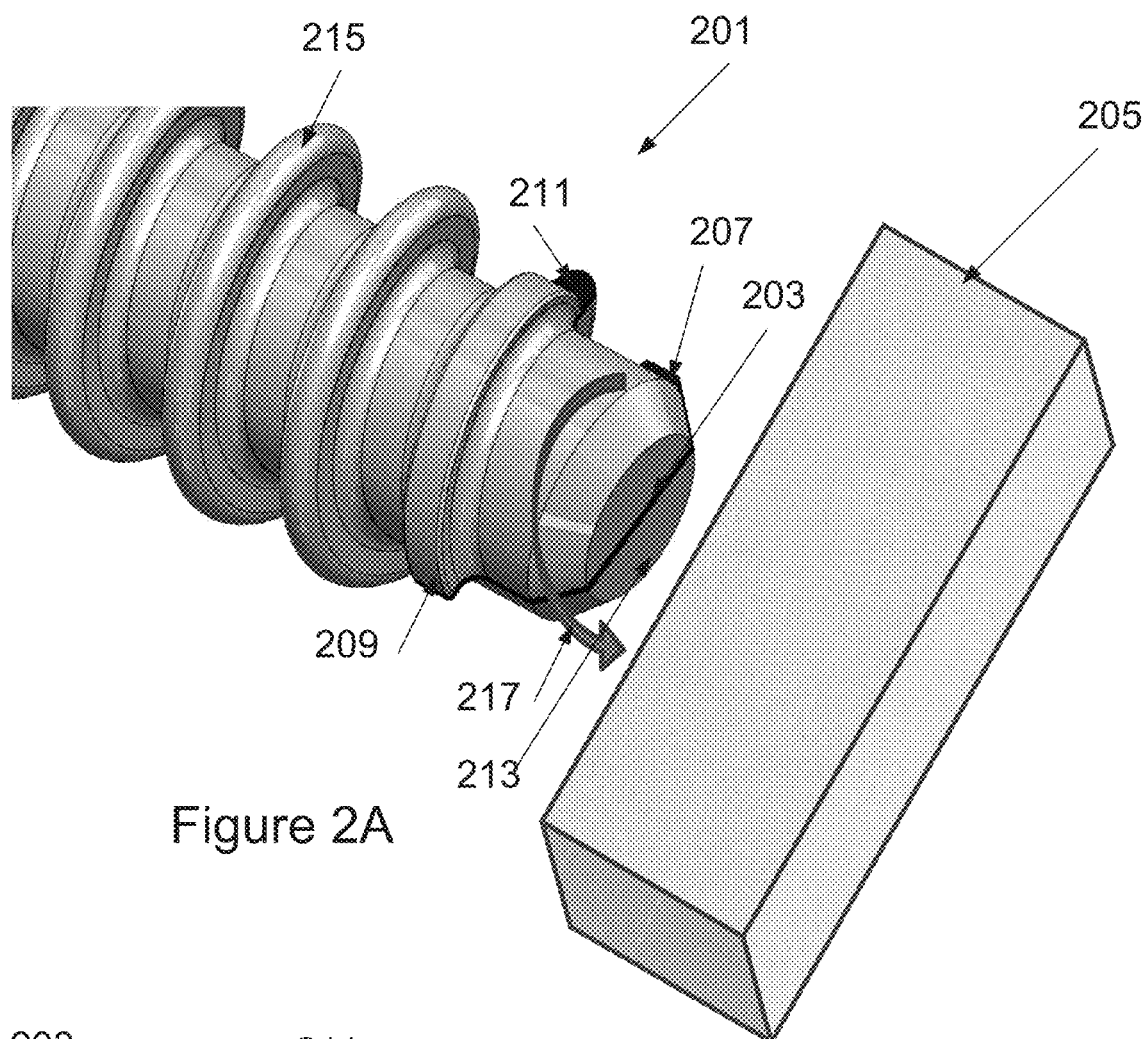
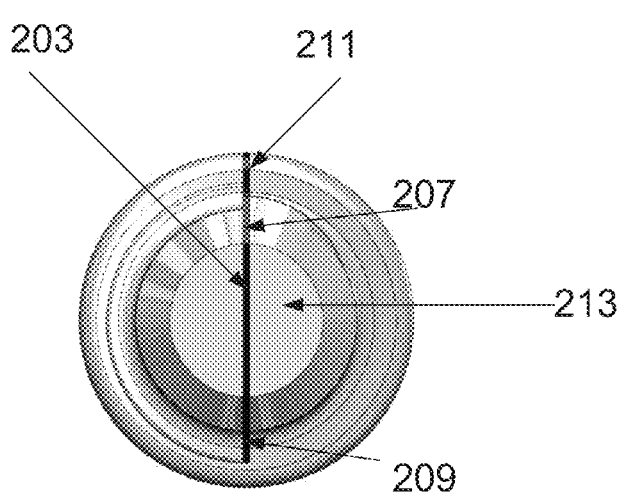
Figure 2A
Figure 2B

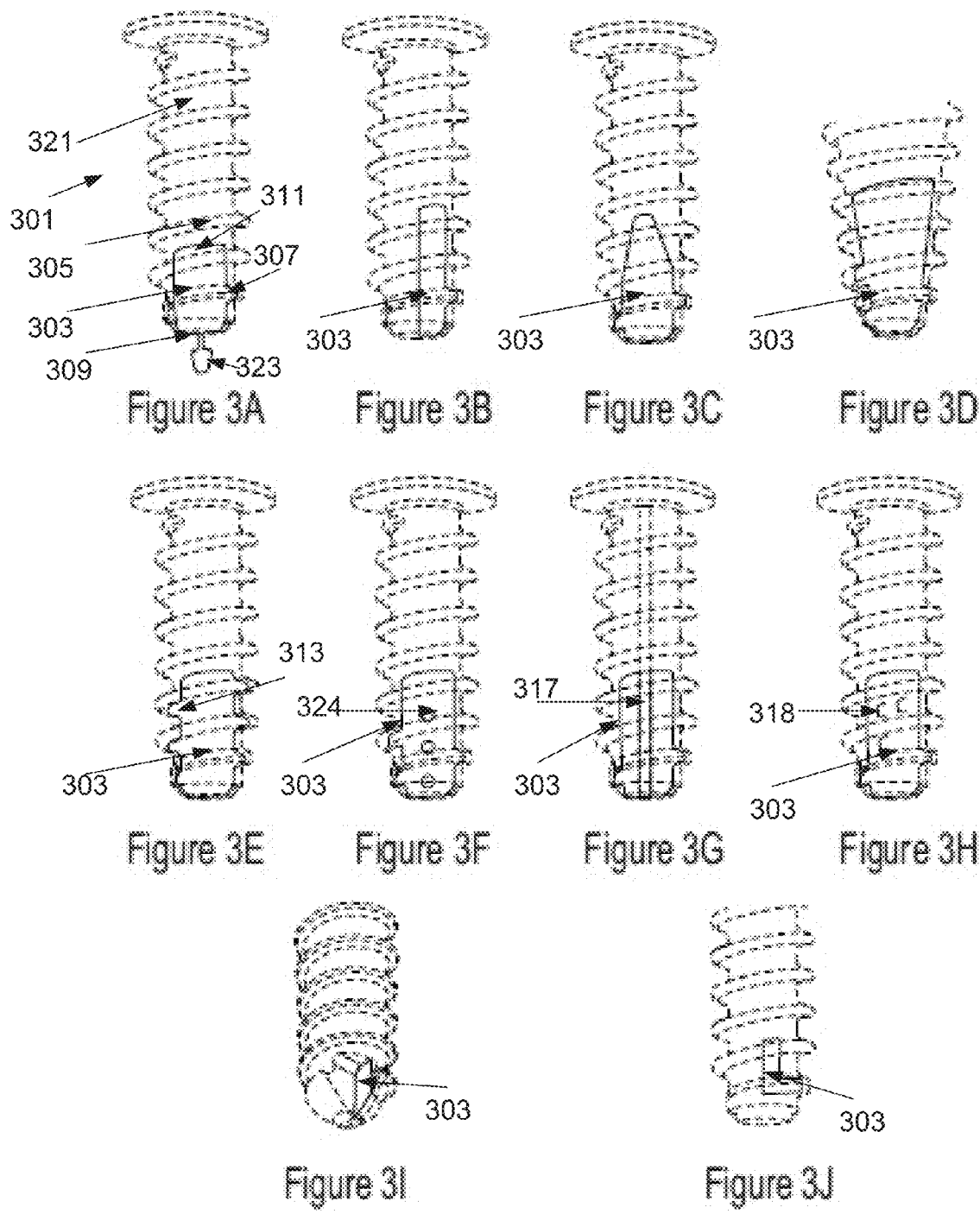

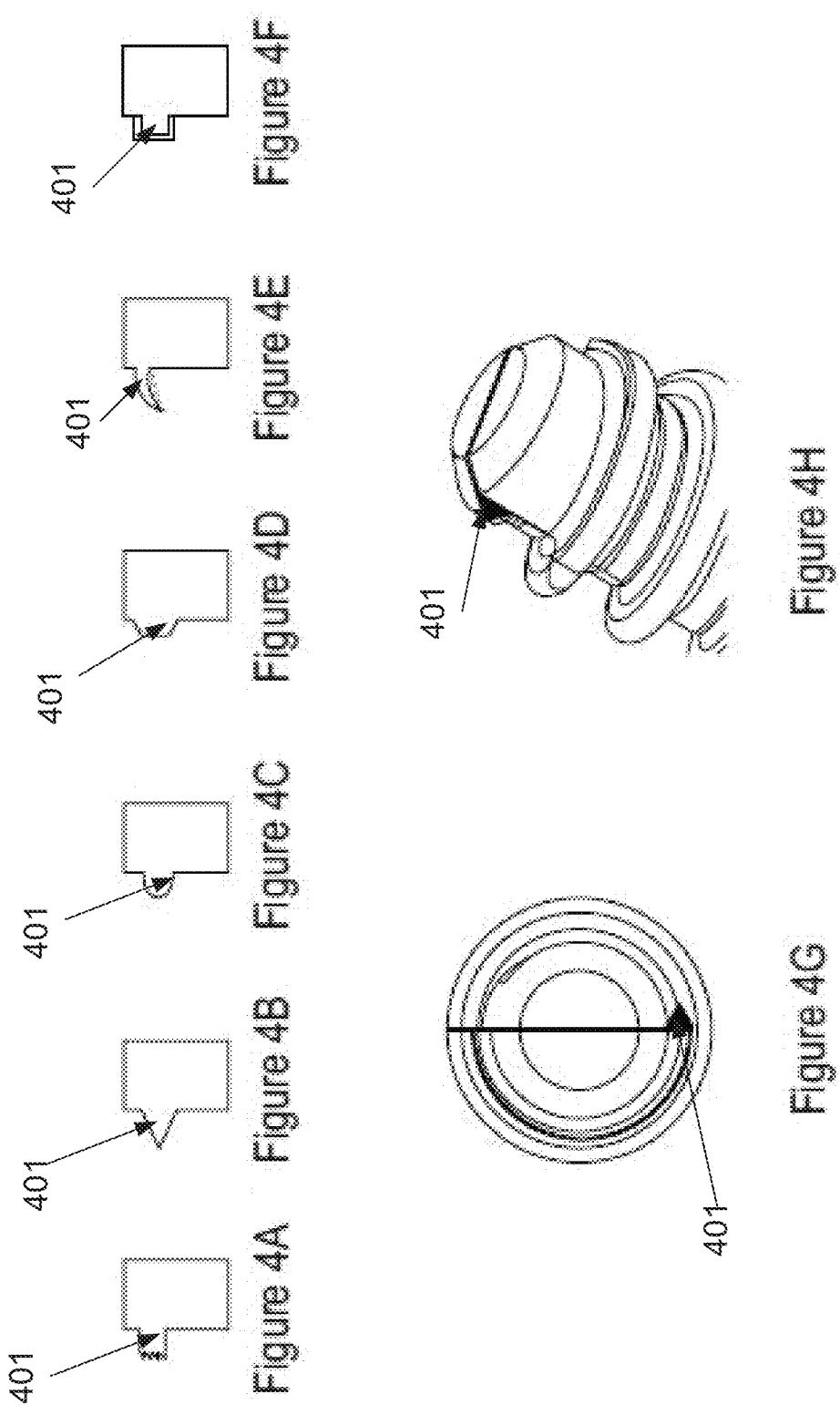

BONE SCREW WITH INSERT

RELATED APPLICATION/S

This application claims the benefit of priority under 35 USC §119(e) of U.S. Provisional Patent Application Nos. 61/617,067 filed Mar. 29, 2012 and 61/641,900 filed May 3, 2012.

This application is also a Continuation-in-Part (CIP) of U.S. patent application Ser. No. 13/742,462 filed Jan. 16, 2013, which claims the benefit of priority under 35 USC §119(e) of U.S. Provisional Patent Application Nos. 61/586,853 filed Jan. 16, 2012, 61/617,067 filed Mar. 29, 2012 and 61/641,900 filed May 3, 2012.

This application is also related to a co-filed U.S. Continuation-in-Part (CIP) patent application titled "Bone Screw Head Design" and having U.S. Ser. No. 13/852,145.

This application is also related to PCT Patent Application Nos. PCT/IB2011/052468 filed on Jun. 7, 2011 and PCT/IB2010/050225 filed on Jan. 18, 2010.

The contents of the above applications are all incorporated by reference as if fully set forth herein in their entirety.

FIELD AND BACKGROUND OF THE INVENTION

The present invention in some embodiments thereof, relates to a screw, more specifically a bone screw, comprising an embedded insert. In some embodiments, the insert serves as a thread cutting tool by covering at least one cutting edge of the screw. Following are disclosures of bone screws (or implants) comprising various bone engaging elements.

US Patent Application Publication Number US20120283790 to Meyer et al. discloses "a surgical bone fixation screw that is improved by a self-guiding end segment that is threadless, elongated and has a smooth outer surface with no cutting edges. The end segment has a length of at least 8 mm and preferably 15 mm and has a bluntly rounded end and an outer contour that is smoothly blended to the threaded shank of the screw. Most preferably, the bluntly rounded end is substantially a prolate hemispheroid".

European Patent Application Number EP1042989 to Venturini et al. discloses "a bone screw with a self-tapping threaded portion which includes at least one constant pitch section comprised of threads having a triangular cusp profile in cross-section and being separated from each other by a shaped bottom land with a concave profile. This allows the elongate conical profile of the threaded portion to be put to best use, and affords a large area of contact with the bone effective to reduce the specific loading pressure."

European Patent Application Number EP 2292176 to Jorneus et al. discloses "A combination of a thread forming tool and an implant is disclosed. The thread forming tool has a thread forming section with a helical thread having at least one cutting surface for cutting a thread in bone. The implant comprises a bone apposition surface having at least one helical thread for position at least partially in the thread of the bone. A longitudinal cross-sectional shape of at least a portion of the helical thread of the thread forming section substantially corresponds to a longitudinal cross-sectional shape of at least a portion of the helical thread of the implant."

SUMMARY OF THE INVENTION

The present invention in some embodiments thereof, relates to a screw, more specifically a bone screw, comprising an embedded insert. In some embodiments, the insert serves as a thread cutting tool by covering at least one cutting edge of the screw.

According to an aspect of some embodiments of the invention there is provided a composite material bone screw comprising an insert, the insert at least partially embedded within the screw. According to some embodiments, a portion of the insert covers at least one cutting edge of the screw. According to some embodiments, the portion is an extension of the insert. According to some embodiments, the insert comprises a plurality of extensions for covering at least one cutting edge intended for self tapping. According to some embodiments, the extension is shaped according to a cross-section of a thread of the screw. According to some embodiments, the extension covers at least a perimeter a cutting edge of the screw. According to some embodiments, the insert is sandwiched between two portions of the screw. According to some embodiments, the insert is flat. According to some embodiments, at least 50% of the surface area of the insert contacts the composite material of the screw. According to some embodiments, the insert extends at least 3 mm along a long axis of the screw. According to some embodiments, the insert extends at least 2 mm along a diameter of the screw. According to some embodiments, the insert extends to the distal tip of the screw. According to some embodiments, the composite material comprising the screw is made of an elongated fiber-reinforced polymer matrix. According to some embodiments, the insert is harder than a cortical bone. According to some embodiments, the insert is harder than the composite material of the screw. According to some embodiments, at least one of the screw and the insert comprises a radiopaque material thick enough for visualizing under fluoroscopy. According to some embodiments, the insert comprises holes extending between opposite faces of the insert. According to some embodiments, the holes are filled with a material of which the screw is made. According to some embodiments, the screw comprises a cutting flute. According to some embodiments, the screw is a lag screw. According to some embodiments, a thin hard foil covers at least 70% of a thread of the screw and does not cover the insert.

According to an aspect of some embodiments of the invention, there is provided a method for embedding an insert within a bone screw using a molding process, comprising providing a mold, placing an insert in the mold, adding composite material to the mold, and molding a screw with an embedded insert. According to some embodiments, placing comprises attaching the insert to the mold using a break-off piece. According to some embodiments, adding comprises filling holes of an insert with the composite material. According to some embodiments, the method comprises machining the screw and the embedded insert to create the thread of the screw.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-B illustrate a distal portion of a bone screw comprising an embedded insert being introduced to a bone, and a front view of the distal end of the screw, according to some embodiments of this invention;

FIGS. 3A-J is a set of various shapes and structures of an embedded insert, according to some embodiments of this invention;

FIGS. 4A-H is a set of various shapes of an extension of an embedded insert, shaped to cover a cutting edge of a bone screw, according to some embodiments of this invention;

DESCRIPTION OF SPECIFIC EMBODIMENTS OF THE INVENTION

Figure 1A:
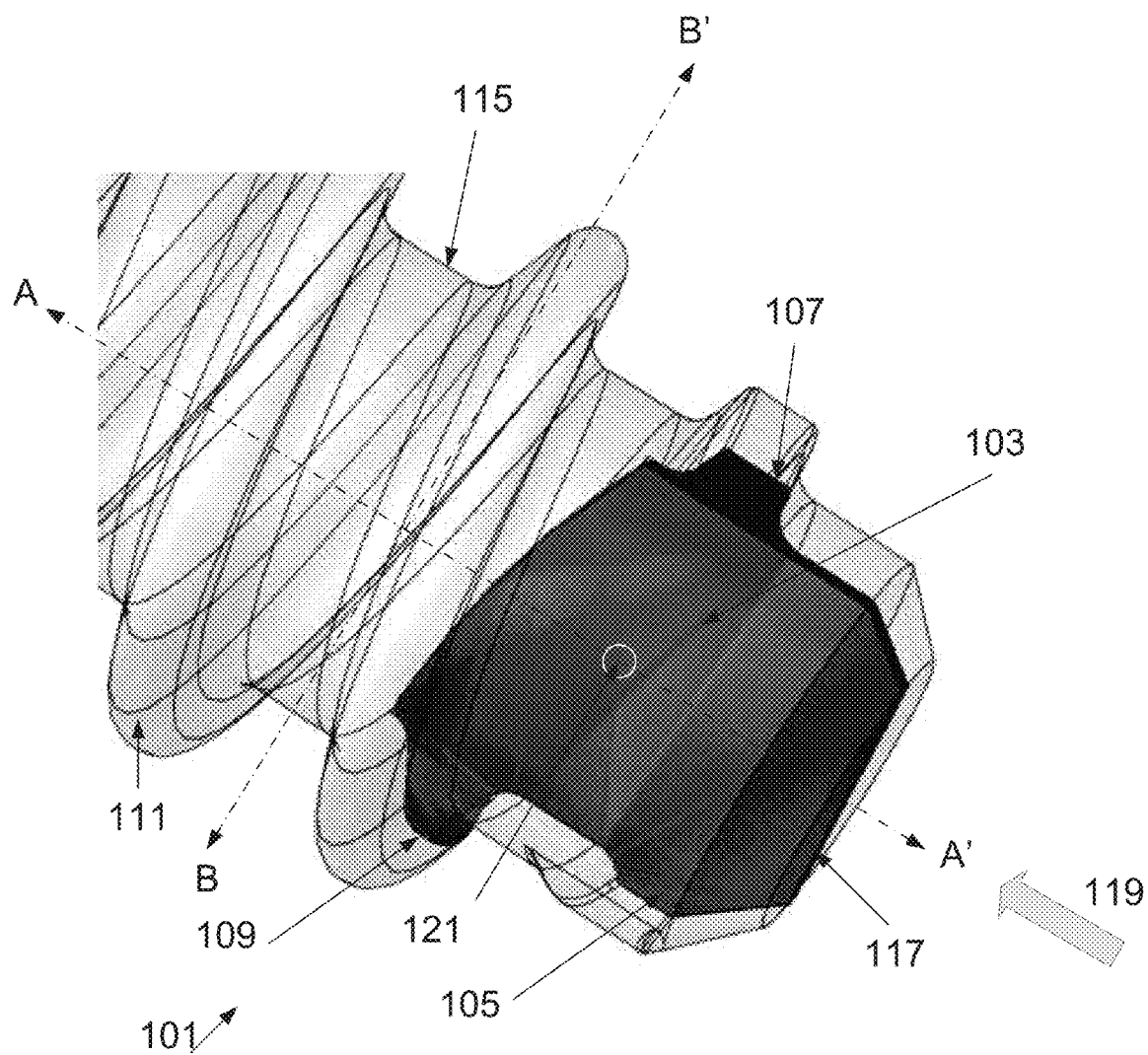
FIGS. 1A-B are front and back view illustrations of a distal portion of a bone screw comprising an embedded insert, according to some embodiments of this invention.

The present invention in some embodiments thereof, relates to a screw, more specifically a bone screw, comprising an embedded insert. In some embodiments, the insert serves as a thread cutting tool by covering at least one cutting edge of the screw.

An aspect of some embodiments of the invention relates to a bone screw comprising an embedded insert. Optionally, the bone screw is a self tapping screw.

In some embodiments, the insert is embedded within a distal portion of the screw. In some embodiments, the insert is embedded within the screw such that it is sandwiched between at least two portions of the screw. In some embodiments, the insert is embedded within the screw such that most of the surface area of the insert (such as at least 60%, 80%, 95% and or intermediate or larger percentages of the surface area) contacts the screw material. In some embodiments, the insert is embedded within the screw such that it is fixed in place in a way that prevents tear off of the insert. In some embodiments, the insert is embedded within the screw by being connected to its interior using adhesion and/or mechanical means.

In some embodiments, the embedded insert and/or extension of it serve as a thread cutting tool during introduction of the screw to the bone. In some embodiments, an extension of the embedded insert covers a cutting edge on the distal end of the screw's thread. Optionally, the insert comprises a plurality of extensions to cover a plurality of cutting edges (such as two or three cutting edges). In some embodiments, the number of cutting edges that are covered by extensions of the insert is the number of cutting edges used for self tapping the screw.

In some embodiments, an extension of an insert is shaped and/or sized according to the shape of a cross section of a tooth of the screw thread. In some embodiments, an extension of an insert is shaped and/or sized such as to fulfill one or more functions that the cutting edge is designed to fulfill, for example cutting a thread in a bone during insertion of the screw into the bone.

In some embodiments, the insert is embedded within the screw such that it is backed by the material comprising the screw. In some embodiments, most of the surface area of the insert is surrounded by the material comprising the screw.

In some embodiments, the insert extends to the distal end of the screw, possibly creating a harder end which may be useful when inserting the screw into the bone.

In some embodiments, the insert is formed as a thin sheet, optionally a sheet of a hard material such as metal or ceramics. In some embodiments, the insert is harder than the material comprising the screw. In some embodiments, the insert is harder than the cortical bone.

In some embodiments, the bone screw is made of a composite material. Optionally, the bone screw is made of longitudinal, relatively parallel reinforcing filaments, within a matrix. In an embodiment, the matrix is a polymer. Optionally, the matrix comprises, in addition to the polymer, chopped fibers of carbon or other reinforcing material.

In some embodiments, the screw and/or insert comprise a radiopaque material for visualizing the screw under fluoroscopy.

An aspect of some embodiments of the invention relates to a method for embedding the insert within the screw. Optionally, the method comprises a compression molding process to embed the insert within the screw.

In some embodiments, a mold is provided and an insert is placed and/or attached to the mold. In some embodiments, a break-off piece is used for attaching the insert to the mold. Optionally, the break-off piece is removed once the screw with its embedded insert is molded.

In some embodiments, the material of the screw is added to the mold, for example surrounding at least a portion of the insert. Optionally, the insert comprises holes, for example holes extending between two opposite faces of the insert, such that the screw material fills those holes upon molding, possibly strengthening the connection between the insert and screw. Optionally, the elongated reinforcing filaments are passed through the holes of the insert.

In some embodiments, the screw may be molded at a first stage, and the insert introduced at a second molding stage. Optionally, a slot may be fabricated and/or machined in the screw molding after the first molding stage, into which the insert is then introduced.

In some embodiments, using compression molding, a rod is produced with the embedded insert. The rod and insert are then machined together, to create the desired thread of the screw.

In some embodiments, the screw is molded, and then a slot is fabricated/and or machined in the screw. The insert may then be introduced to the slot and attached to the screw by adhesion means and/or mechanical connections, for example using small pins.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1B:
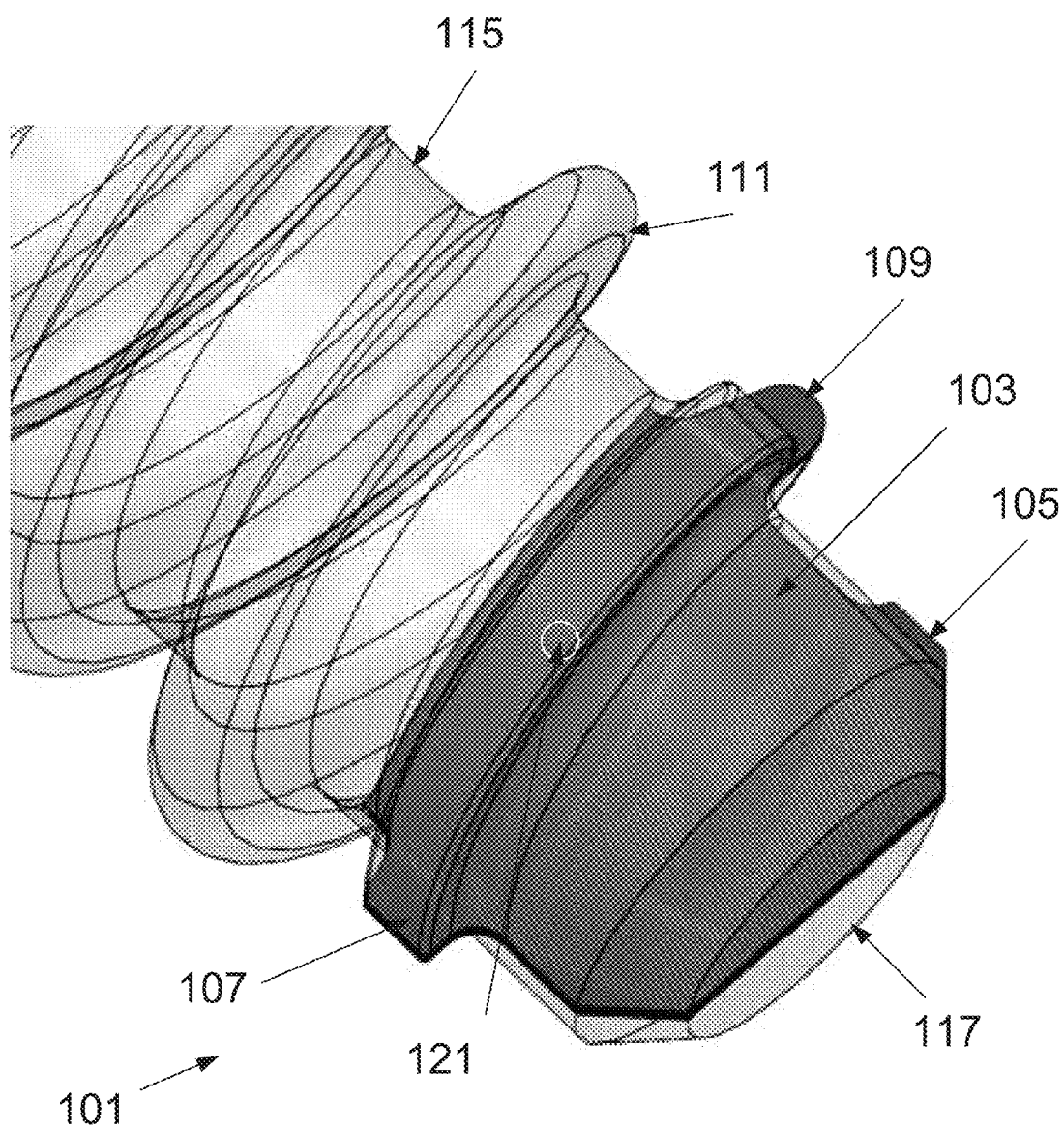

General Description of a Screw with an Embedded Insert, According to Some Embodiments of the Invention Referring now to the drawings, FIGS. 1A-B are front and back view illustrations of a distal portion of a bone screw 101 comprising an embedded insert 103, according to an exemplary embodiment of this invention. In some embodiments, a bone screw comprises a head (not shown in this figure), a cylindrical rod 115, a thread 111 covering at least a portion of cylindrical rod 115, a distal end 117, and one or more cutting edges 105-109 which will be further referred to.

In some embodiments, the bone screw is made of a composite material. Optionally, the screw is made of longitudinal, relatively parallel reinforcing filaments, such as carbon filaments, within a matrix such as PEEK (polyetheretherketone) or PEKK (polyetherketoneketone).

In some embodiments, the screw or a portion of it such as distal portion 101 comprises a component used for interacting with the bone, such as a leading edge of a thread. In some embodiments, the screw is a self tapping screw. Optionally, the self tapping screw includes one cutting edge, for example cutting edge 105. Optionally, the self tapping screw includes a plurality of cutting edges, such as cutting edges 105 and 109, which may be used to cut a thread and/or a hole in the bone as the screw is driven into the bone.

In some embodiments, the interacting component of the screw comprises a cutting flute located at the distal end of the screw. Optionally, a portion of the flute creates a hole in the bone during insertion, and another portion cuts a thread in the bone, such as to enable the insertion of the rest of the screw, as will be further explained in FIG. 6.

In some embodiments, the insert comprises one or more extensions that are shaped and/or sized to cover an interacting component such as a cutting edge of a screw. Optionally, the extension is shaped according to the shape of a cross section of a tooth of the screw thread. For example, as shown in this figure, three extensions of insert 103 having trapezoidal like shapes extend externally to rod 115 such that they cover cutting edges 105, 107 and 109, configured on the distal end of thread 111.

In some embodiments, insert 103 is formed as a thin sheet, optionally a sheet of a hard material such as metal.

In some embodiments, the insert extends to the distal end of screw 117 such that at least a portion of insert 103 contacts the bone during initial contact.

In some embodiments, insert 103 is embedded within screw 101 such that it is backed by the composite material of the screw. Optionally, during normal use of the screw, leading cutting edge 105 covered by insert 103 may be the first to contact the bone, and force exerted by the bone (shown by arrow 119) may be first absorbed by insert 103. In some cases, by covering one or more cutting edges of the screw, the embedded insert may reduce damage that would otherwise have occurred, for example to the thread of the screw during insertion to the bone.

In some embodiments, if insert 103 transverses a cross section at the distal end 117, as shown in this figure, force 119 may push the insert against the surrounding screw material in a way that possibly increases the connection strength between the screw and the insert, as opposed to causing tear-off of the insert from the screw.

Structural Description of an Insert Embedded within a Screw, According to Some Embodiments of the Invention In some embodiments, insert 103 is embedded within distal portion 101 such that most of the insert (for example at least 60%, 80%, 95% or intermediate or larger values) is firmly enclosed within the material forming the screw, for example insert 103 may be sandwiched between two portion of the screw. In some embodiments, insert 103 is embedded within screw 101 such that it is fixed in place in a way that prevents it from tearing off.

In some embodiments, insert 103 is embedded within screw 101 by being connected to its interior using, for example, pins, such as pin 121. Optionally, one or more pins may connect insert 103 to distal portion of screw 101 in various locations, for example along a longitudinal axis of the screw, along a perimeter of insert 103, etc. Optionally, pin 121 is made of titanium and/or titanium alloy.

In some embodiments, faces and/or edges of insert 103 are surrounded by the screw's material. Optionally, most of the surface area of insert 103, such as at least 60%, 80%, 95% or intermediate or larger values contacts the screw material. Optionally, at least one face of insert 103 contacts the screw material. Optionally, as shown in this figure, two faces such as opposite faces of insert 103 contact the screw material.

In some embodiments, one or more faces of insert 103 contact the screw material along a longitudinal axis AA' of the screw, extending for example between the head of the screw (not shown in this figure) and the distal end 117. Optionally, insert 103 transverses rod 115 longitudinally, such that a segment of half cylinder of rod 115 contacts one side of insert 103, and a segment of the second half cylinder contacts the opposite side of insert 103, sandwiching the insert in-between.

In some embodiments, insert 103 extends longitudinally within the interior of the screw, for example extending to at least 5%, 20%, 40%, or 70% or intermediate or larger values of the total length of the screw. Optionally, the length of the insert along a longitudinal axis is determined according to the pitch of the thread and\or the number of cutting edges that are covered by extensions of insert 103. For example, if the pitch of thread 111 is 2 mm, and insert 103 covers the 3 cutting edges at the distal portion of the screw, then the length of the insert may be 6 mm. In another example, insert 103 may extend half way through the total length of the screw, beginning at the distal tip 117 and extending in a proximal direction towards the head of the screw, for example to a distance of at least 3 mm, 5 mm, 30 mm or intermediate or larger distances. Optionally, the total length of the screw ranges between 10 mm-120 mm.

In some embodiments, insert 103 extends along a horizontal axis BB', optionally being a short axis of the screw. Optionally, insert 103 extends horizontally such that it fully transverses the screw, for example extending along a diameter of thread 111 in some portions, and along a diameter of rod 115 in other portions. Optionally, insert 103 may extend at least 20%, 50%, or 80% or intermediate or larger values of the diameter of rod 115 and/or a major diameter of thread 111 (i.e. largest diameter) and/or a pitch diameter of thread 111 (i.e. a diameter measured between the rod diameter and the major diameter), along the horizontal axis. In one example, a typical major diameter of a screw may range between 3-15 mm.

As previously noted, one or more extensions at a distal portion of insert 103 may be shaped and/or sized to overlie one or more cutting edges such as 105, 107, 109. Optionally, the extension aligns the cutting edge. Optionally, an extension of the insert which covers a cutting edge may be rectangular, triangular, trapezoidal (as shown in this figure) or any other shape that fully aligns the cutting edge, possibly determined according to a cross section of a tooth of thread 111, as will be further shown in FIG. 4. In some embodiments, the distal extension of insert 103 may extend beyond the perimeter of cutting edge 105, such as extending at least 0.3 mm, 0.7 mm, or 1.3 mm or intermediate or smaller distances beyond the perimeter of the cutting edge, for example to provide a sharper and/or harder edge that may facilitate cutting through a bone.

In some embodiments, insert 103 may cover the cutting edge of a few (e.g. one, two, three and/or four) teeth at the distal end of thread 111. In some embodiments, insert 103 covers the cutting edges of all teeth that are intended for self tapping the screw. Optionally, the number of cutting teeth intended for self tapping (optionally covered by insert 103) relative to the number of other thread teeth should be such that allows self tapping on one hand but does not compromise the thread ability to provide firm fixation of the screw to the bone on the other hand.

In some embodiments, cutting teeth such as 105, 107 and 109 at the distal end of thread 111, which may be protected by extensions of insert 103, have different sizes. Optionally, the height of the teeth, as measured in a radial direction in relevance to rod 115, increases, in a manner that the shortest cutting tooth (105) is located in the vicinity of the screw's distal end 117. For instance, where three cutting teeth are available, as shown in this figure, the most distal one is one third the height of complete tooth of thread 111, the second tooth is two thirds the height of a complete tooth, and the third tooth has a height of a complete tooth. In such a case, insert 103 may include one, two, or three extensions. Optionally, the extensions are sized and/or shaped to align the cutting edges of the teeth, such that the most distal extension extends to one third of a height of a complete tooth, the second extends to two thirds of a height of a complete tooth, and the third extends to a full height of a tooth.

In some embodiments, insert 103 has a geometry suitable for engaging components of the screw such as rod 115 and/or thread 111. Optionally, insert 103 conforms with the profile of thread 111, such that it does not extend externally to the thread. Optionally, insert 103 includes extensions that are sized and/or shaped to cover cutting edges on the distal end of thread 111, and/or includes extensions that are sized and/or shaped to fit within some or all the rest of the teeth of thread 111.

In some embodiments, insert 103 is sized only to cover a cutting edge, and does not extend beyond a surface of the cutting edge, for example does not extend within the interior of the screw. In one example of such a case, the insert covers a surface of a cutting edge and is connected to the cutting edge using adhesion and/or mechanical means, such as pins.

In some embodiments, insert 103 may cover, for example, 2-10% of the external surface area of the screw.

In some embodiments, the portion of insert 103 which covers a cutting edge may not fully cover the surface of the cutting edge, for example comprising a hole.

In some embodiments, an axial distance between adjacent extensions such as 105 and 109 is sized according to the axial pitch of thread 111. Optionally, a distance between opposite ends of extensions of insert 103, such as 105 and 107 (along the horizontal axis) is determined according to the major (i.e. largest) diameter of thread 111.

In some embodiments, insert 103 is formed as a thin sheet. Optionally, the thickness of the insert ranges between 0.1 mm-0.5 mm. In some embodiments, the thickness of insert 103 may change, for example change along a longitudinal axis. Optionally, the thickness gradually decreases such that a distal portion of the insert is thicker than a proximal portion. Optionally, a thick distal end of the insert provides a harder front end at the screw's tip, which may facilitate driving the screw into the bone, as shown in the following figure.

In some embodiments, at least one portion of insert 103, for example an extension, may have a certain volume such as to fit in various components of the screw. For example, an extension of insert 103 may be shaped in a rounded conical form, such as to fit within the interior of a thread tooth having a similar profile.

In some embodiments, at least a portion of insert 103 is shaped as a cylinder. Optionally, the whole insert is shaped as cylinder, for example extending within an interior distal portion of rod 115.

In some embodiments, for example if the screw is formed as a conical screw, insert 103 may have a geometry suitable for engaging the conical screw, for example increasing in width in a proximal direction, as will be shown in FIG. 3.

In some embodiments, for example if the screw is not self-tapping and does not include a cutting edge, insert 103 may be embedded within rod 115 and/or thread 111 to further strengthen the screw and possibly prevent wear, for example wear to the distal end 117 during insertion of the screw to the bone.

Exemplary Materials of a Screw and an Embedded Insert

As previously noted, in some embodiments the screw is made of a composite material. Optionally, the screw made of longitudinal, relatively parallel reinforcing filaments, within a matrix. In an embodiment, the matrix is a polymer. In an embodiment, the matrix comprises, in addition to the polymer, chopped fibers of carbon or other reinforcing material. Optionally, the content of the reinforcing elements within the composite material is increased, in order to strengthen the material. In an exemplary embodiment of the invention, carbon fiber reinforced polymer (such as PEEK or PEKK) is used for the bone screw.

In an embodiment, the carbon fibers volume content is about 60%. In an embodiment, the carbon fibers volume content is about 70%, optionally 80% or higher. In an embodiment, prepreg tapes of carbon fiber reinforced polymer are produced with about 60% carbon fiber content. Additionally and/or alternatively, the prepreg tapes are produced with carbon fiber contents of, for example, approximately 60%, and then later, part of the polymer is extracted outside from the tapes, optionally using high pressure and temperature.

In some embodiments, the screw comprises a core of straight longitudinal reinforcing filaments. In some embodiments, the orientation of the fibers in thread 111 complies with that of the thread pitch. In some embodiments, rod 115 s formed of a core with straight longitudinal fibers, and thread is formed of folded longitudinal fibers.

In some embodiments, insert 103 is made of a hard material, such as metal (for example titanium alloy, e.g. Ti-6Al-4V), ceramics (such as zirconia) and/or other hard materials. Optionally, the insert may be formed of a composite material, for example a material having a carbon volume content that is different from the carbon volume content in the material in which the rest of the screw is formed of.

In some embodiments, insert 103 is harder than the cortical bone. In some embodiments, insert 103 is harder than the composite material of the rest of the screw. In some embodiments, insert 103 is made of a material having the same hardness as the rest of screw, but with less inclination to crumble and and/or having less visible crumbs.

In some embodiments, the screw is formed of carbon fiber reinforced polymer, a material that is radiolucent under imaging such as fluoroscopy. Optionally, insert 103 is formed of a radiopaque material, such as Tantalum. Additionally or alternatively, a radiopaque marker may be added to the screw and/or insert 103 in order to provide for visualization of the screw under fluoroscopy during operation and/or at follow-up. In some embodiments, radiopaque markings include dots, lines, etc.

In some embodiments, for example when imaging techniques such as MRI are used, insert 103 may be made of ceramics such as zirconia, which does not interfere with MRI.

Interaction Between a Bone and a Bone Screw Comprising an Embedded Insert, According to Some Embodiments of the Invention FIG. 2A-B illustrate a distal portion of bone screw 201 comprising an embedded insert 203 being introduced into bone 205 (FIG. 2A), and a front view of a distal end of the screw 213 (FIG. 2B), according to an exemplary embodiment of this invention.

The bone screw, optionally self tapping, may be used, for example, to secure a bone plate (not shown in this drawing) to bone 205.

In some embodiments, as distal portion 201 followed by the rest of the screw is driven into bone 205, cutting edges 207, 209, 211 which are optionally covered by insert 203 cut a thread within bone 205, allowing the threading of the rest of screw 201 into bone 205.

In some embodiments, a pilot hole is drilled in bone 205 before screw 201 is introduced to bone 205. Alternatively, a pilot hole is not drilled in bone 205, for example if screw 201 is a self tapping screw. Optionally, if the screw is self tapping, a pilot hole may be drilled, if at all, to a diameter smaller than the major diameter, for example. Optionally, if the self tapping screw comprises an insert, a potential advantage of the insert may be the option of creating a pilot hole smaller than the pilot hole that would have been drilled without the insert, for example because the insert is harder than the screw and would therefore facilitate cutting a hole through the bone.

In some embodiments, during insertion to the bone, the distal end 213 contacts bone 205 to further penetrate it, and the first cutting edge 207 is rotated in the direction shown by arrow 217 such as to cut a thread through bone 205.

In some embodiments, distal tip may comprise a cutting flute (not shown in this figure). Optionally, at least a portion of the cutting flute is covered by the insert, as will be further explained in FIG. 6.

In some embodiments, insert 203 extends within distal portion of screw 201 in a way that it is perpendicular to the surface of bone 205, therefore being configured along the axis of rotation of the screw. As insert 203 may be harder than the cortical bone, a potential advantage may include decreasing the amount of torque force that needs to be applied to the head of the screw during threading (and/or unthreading), for example in comparison to a screw that does not comprise an embedded insert.

Another potential advantage of a screw with an embedded insert may include increasing the screw's resistance to forces such as shear forces. For example, the screw may be made of a non-isotropic, composite material, which may have lower resistance to shear forces, for example compared to metal. In such a case, thread 215, for example, may be susceptible to damage (e.g. breakage or tear). Optionally, insert 203 may be formed of a hard, isotropic material such as metal, and by being incorporated into at least a portion of thread 215 and/or distal end 213, insert 203 may increase the overall resistance of screw 201, for example preventing wear of distal end 213 such as during initial penetration into bone 205. Optionally, due the hardening of distal end 213 by insert 203, the amount of debris originating from drilled bone 205 and/or from the screw may be reduced.

In some embodiments, the modulus of elasticity of the composite material in which the screw is formed of is close to that of a cortical bone. A potential advantage of the screw having a similar modulus of elasticity to the cortical bone may include lowering the risk for occurrence of stress risers in bone 205 and/or in the screw. Optionally, by extending across a short axis and/or a long axis of the screw, insert 203 contributes to the distribution of stress, possible preventing stress risers as well.

In some embodiments, mechanical and/or biomechanical properties of the screw as a whole, such as bending strength, may be affected by the material and/or size and/or shape of insert 203.

Various Shapes and Sizes of Inserts Embedded within Screws, According to Some Embodiments of the Invention FIGS. 3A-J is a set of various shapes, sizes and/or structures of an embedded insert, according to some embodiments of this invention. For clarity, each embedded insert 303 described in this drawing is shown inside an outline of a screw 301, marked by the dotted line. Optionally, other shapes of screws and/or screw-insert combinations may be used.

In some embodiments, insert 303 is a thin sheet, for example having a thickness of 0.1 mm. In some embodiments, the insert may have a thickness of, for example, 0.5 mm, 1 mm, 3 mm or any larger and/or intermediate thickness. In some embodiments, the thickness of the insert gradually changes, for examples decreases along a longitudinal axis. In some embodiments, an extension of the insert may be thicker than other portions of the insert, or vice versa. In some embodiments, the thickness may change according to a shape of the thread. In some embodiments, the thickness may be determined according to a diameter of the screw, for example the major diameter, for example being ¼ of the screw diameter.

FIG. 3A shows insert 303 having a rectangular shape. The insert comprises one extension 307, located on the distal end of an edge of the insert. Extension 307 may be sized and/or shaped to cover, for example, a leading cutting edge on the end of thread 305. Optionally, extension 307 may be square shaped, triangular shaped, or trapezoidal shaped, for example according to the shape of the cross section of a tooth of the screw's thread, as will be shown in the next figure.

Different embodiments may use different lengths of an insert. In this figure, distal end 309 of insert 303 extends to the distal end of screw 301. Proximal end 311 extends along a longitudinal axis of the screw, for example to a distance equal to a third of the total length of screw 301. Optionally, the length of an insert is determined according to the number of cutting teeth intended to be covered, and/or according to the thread pitch.

In some embodiments, screws may comprise inserts with various widths. Optionally, as shown in this figure, insert 303 extends horizontally within screw 301 to cover a full diameter of rod 321.

In some embodiments, during manufacturing of the screw, insert 303 may comprise a break-off piece 323 used, for example, for attaching the insert to a mold. Optionally, break-off piece 323 is positioned externally to screw 301, to allow removal of the break off piece once screw 301 is molded and insert 303 is embedded within it.

FIG. 3B shows insert 303 having a rectangular distal end 309, and a proximal end 311 extending to a longer distance (for example longer than the insert described in 3A) along the longitudinal axis of screw 301 in the proximal direction. Optionally, insert 303 extends horizontally within screw 301 to cover half of a diameter of rod 321.

FIG. 3C shows insert 303 having a rectangular distal end 309, a narrowing proximal end 311, and two opposite trapezoidal extensions 307. Optionally, the distance between the ends of extensions 307 (measured along the horizontal axis) is determined according to the pitch diameter and/or the major diameter of thread 305.

FIG. 3D shows insert 303 having a narrow distal end 309 and a body that increases in width towards the proximal end 311. Optionally, an insert of this shape or similar may be embedded in a conical screw. The insert describes in this figure includes three extensions 307. Optionally, the distance between adjacent extensions 307 which are positioned on the same edge of insert 303 is determined according to the axial pitch of thread 305.

FIG. 3E shows insert 303 having two extensions 307 shaped and/or sized to cover cutting edges, and 4 extensions 313 shaped and/or sized to fit within full sized teeth (or crests) of thread 305. Optionally, extensions may have a square shape, triangular shape, or trapezoidal shape, for example according to the shape of the cross section of the teeth of thread 305. Optionally, the height of the extensions (the distance to which an extension extends) increases, such that the most distal extension is the shortest, according to the height of the cutting teeth which increases until reaching the height of a full sized tooth of the thread.

FIG. 3F shows insert 303 comprising a plurality of holes 324. Optionally, the holes extend between two opposite faces of the insert, such that the material in which the rest of screw 301 is formed of exists within the holes of insert 303. Optionally, the described configuration further strengthens the connection between insert 303 and screw 301.

FIG. 3G shows insert 303 comprising a channel 317, dimensioned for example to pass a wire through. Optionally, screw 301 may be cannulated, and a wire and/or suture passed within screw 301 may pass within the channel of embedded insert 303 as well. In one example, cannulated screw 301 and/or insert 303 may be inserted over a K-wire.

FIG. 3H shows insert 303 comprising protrusions 318. Optionally, the composite material forming screw 301 fills spaces between the protrusions, possibly further strengthening the connection between insert 303 and screw 301. In some embodiments, insert 303 may be textured, for example to create stronger adhesion to the screw material.

FIG. 3I shows insert 303 dimensioned to cover a cutting flute at the distal tip of screw 301. Optionally, insert 303 covers a portion of the flute. Optionally, the insert is limited to the flute portion, and does not extend to other components of the screw.

FIG. 3J shows insert 303 dimensioned such that only an extension of the insert covers a cutting edge of the screw, and the rest of the insert does not contact any external edge, face, and/or surface of the screw.

Various Shapes and Sizes of Extensions of an Embedded Insert for Covering Cutting Edges of Bone Screws, According to Some Embodiments of the Invention FIGS. 4A-F are a set of various shapes of an extension of an embedded insert, shaped to cover an interacting edge of a bone screw, according to some embodiments of this invention. Optionally, an interacting edge includes any cutting edge and/or cutting flute of a screw which contacts and/or interacts with the bone during insertion of the screw, for example cutting a thread through the bone.

For clarity, a top view of the insert comprising the extension is shown in this figure. Optionally, various combinations of inserts (such as the inserts presented in FIG. 3 above) and one or more extensions presented in this figure may be used.

In some embodiments, extension 401 of an embedded insert is shaped and/or sized according to a shape and/or size of a cross section of the thread teeth.

In some embodiments, extension 401 of an embedded insert is shaped and/or sized such as to fulfill one or more functions that the cutting edge and/or flute is designed to fulfill.

FIG. 4A shows extension 401 of an embedded insert having a saw-blade like edge, which may be used, for example, to cut through a bone when the screw is introduced to the bone.

FIG. 4B shows extension 401 of an embedded insert having a triangular shape with a sharp tip, which may be used, for example, to split a portion of a bone when the screw is introduced to the bone.

FIG. 4C shows extension 401 of an embedded insert having a rounded blunt tip, which may be used, for example, to create a channel-like thread in the bone when the screw is driven into the bone.

FIG. 4D shows extension 401 of an embedded insert having a trapezoidal shape, which may be used for cutting through the bone.

FIG. 4E shows extension 401 of an embedded insert having a thick three dimensional rounded conical shape, which may be used for example to fit within a volume of a thread having a similar profile. One of the reasons for using a thick three dimensional extension is, for example, the non-flat contact created between the three dimensional extension and the backing part of the thread, which may better distribute stress.

FIG. 4F shows extension 401 of an embedded insert having a thick three dimensional cuboidal shape, which may be used for example to fit within a volume of a thread having a similar profile. In this example, a thickness of the extension may range between, for example, 0.5 mm-3 mm.

FIG. 4G is a front view of a distal end of a screw, comprising an embedded insert with a triangular extension

401, for example the extension of FIG. 4B, covering a cutting edge of the screw having a similar profile.

FIG. 4H is a side view of a distal portion of a screw, for example the screw of FIG. 4G, showing a triangular extension 401 covering a leading cutting edge of a screw.

Embodiments of a Self Tapping Bone Screw Comprising an Embedded Insert

Figure 5A:
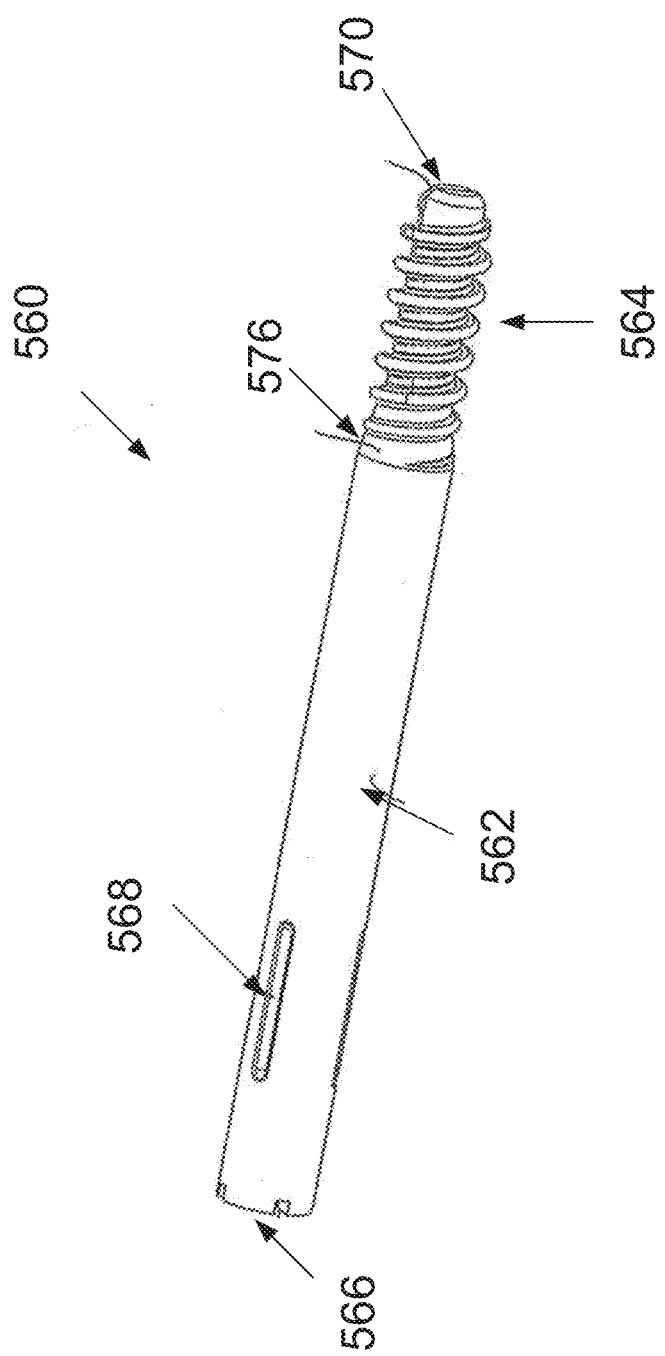
FIGS. 5A-C are illustrations of a composite material femur lag screw comprising an embedded insert, according to an exemplary embodiment of this invention.
Figure 5B:
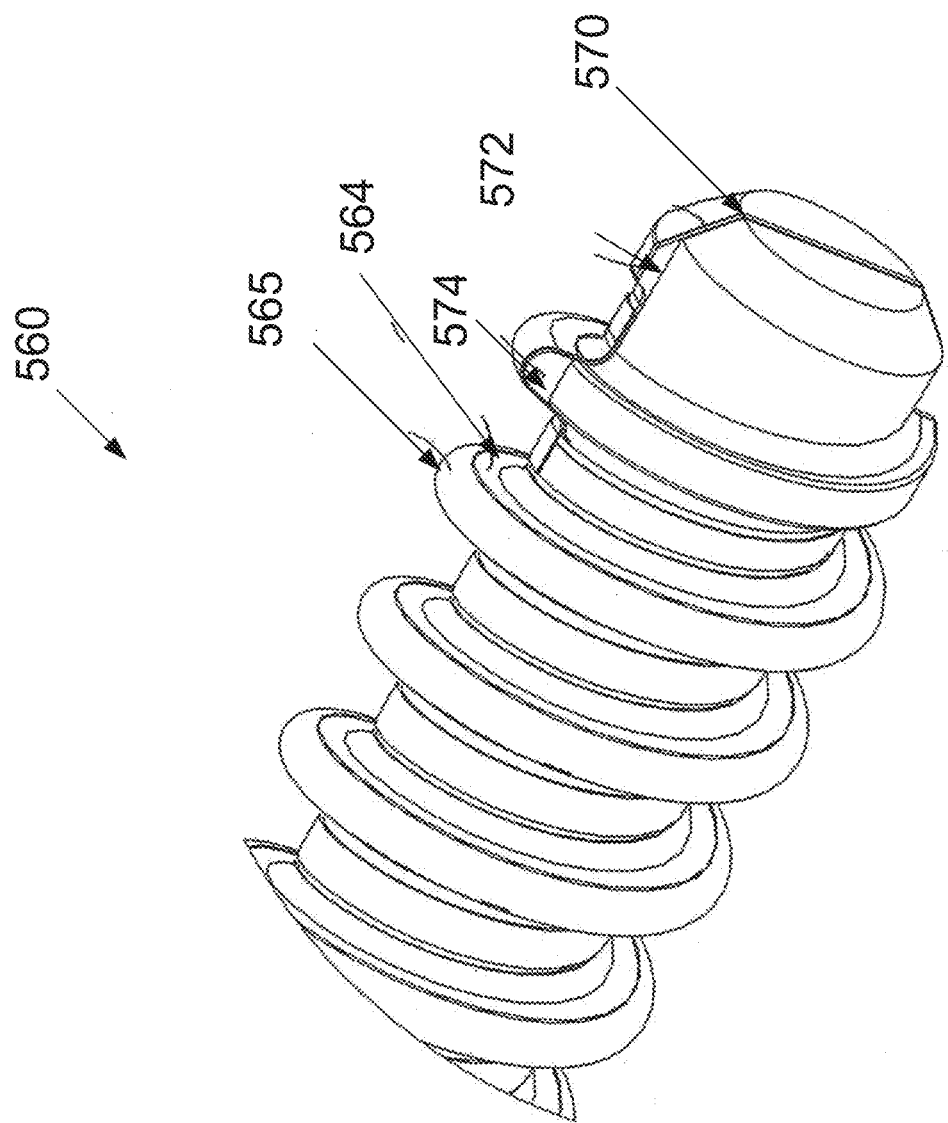
Figure 5C:
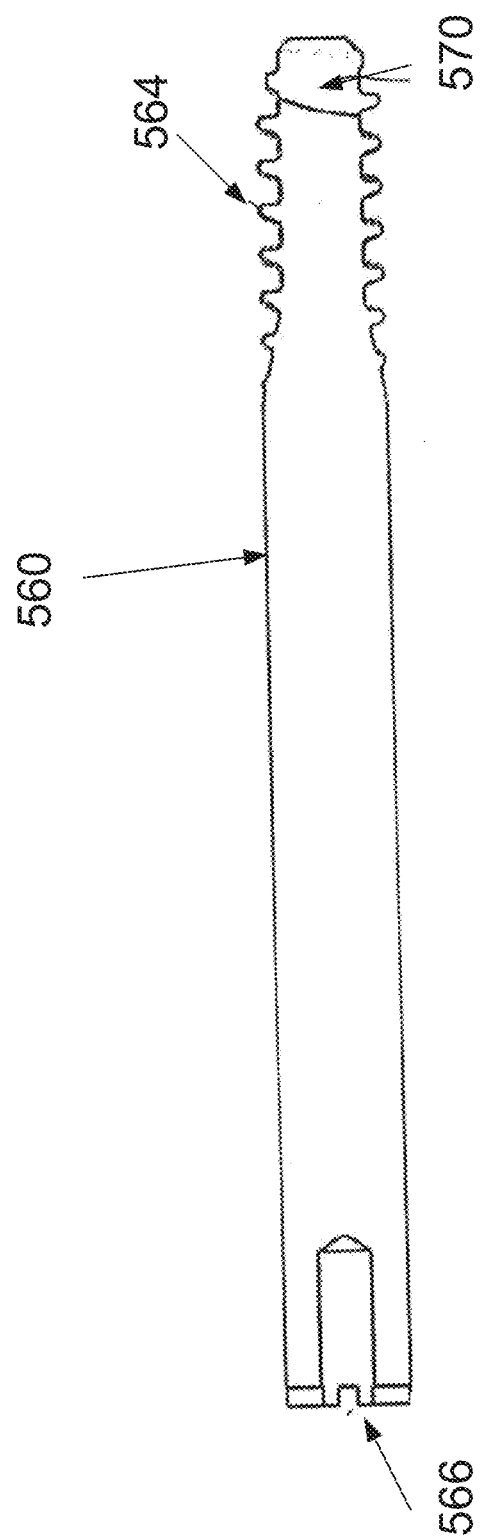

FIGS. 5A-C illustrate some embodiments relating to a composite material lag screw comprising an embedded insert. The lag screw may be implanted in conjunction with a proximal femoral nail to treat fractures at the proximal region of a femoral bone. The composite material lag screw 560 which is inserted into the femoral neck and head is composed of polymer and fibers as previously described, for example of PEEK reinforced with carbon fibers.

It is noted that the inventors of this invention have successfully tested a few composite material lag screws with various insert thicknesses for their self-tapping capability in a hard, non-osteoporotic bone.

Lag screw 560 comprises a shank 562 and a threaded distal portion 564 to provide for a firm fixation within the femoral head bone. At its proximal end, lag screw 560 includes connection means 566 configured to engage with a designated instrumentation, to assist in lag screw insertion and removal (in case required). In addition, lag screw 560 comprises a slot 568 at its proximal portion, intended to enable limitation of lag screw sliding and rotation.

The distal section of lag screw thread 564 is of self-tapping type. Optionally, insert 570 is incorporated into lag screw 560 distal end. A potential advantage of embedded insert 570 may include improving lag screw self-tapping capability upon introduction into the bone and/or preventing potential damage to lag screw distal end. Optionally, insert 570 is formed as thin sheet.

FIG. 5B is a magnification of the distal end of lag screw 560. Two opposite faces of insert 570 contact the screw interior along a longitudinal segment such that insert 570 is sandwiched between the two portions. As shown in this figure, insert 570 transverses the rod and/or thread of screw 560, extending along a full diameter of the rod in some portions and a full diameter of the thread in other portions.

FIG. 5C is a longitudinal cross section of lag screw 560. Insert 570, located at the distal end, comprises three extensions for covering three cutting edges at the thread distal end. The extensions are configured along the insert in a manner that two extensions are located on the right edge of the insert, and another extension is located on the left edge of the insert, along a horizontal axis. Two cutting teeth 572, 574, shown in FIG. 2B, which are covered by insert 570, gradually increase in height as previously described, in a manner that the smallest, 572, is located in the vicinity of screw distal end.

In some embodiments, as previously detailed, a radiopaque marker (not shown in the figure) may be incorporated into the lag screw 560 and/or insert 570 to enable visualization under fluoroscopy.

In some embodiments, as previously detailed, lag screw 560 and/or insert 570 are cannulated, for example to allow their insertion over a K-wire (not shown in the figure).

In some embodiments, a thin foil 565, which may be made of material with higher hardness than cortical bone, coats most of the screw thread 564, such as to increase the hardness of the coated component. Optionally, foil 565 does not coat the distal end of the thread, comprising the self tapping teeth which covered by insert 570. Optionally, foil 565 also covers tapper portion 576, between the lag screw shank 562 and thread 564. Optionally, foil 565 may be made of, for example, metal such as pure titanium or titanium alloy (e.g., Ti-6Al-4V). The thickness of the foil may be, for example, 0.01 mm-0.1 mm.

In some embodiments, insert 570 and foil 565 are made of the same material. Optionally, a single component such as a sheet of metal comprises the insert and foil together.

In some embodiments, foil 565 may be applied to cover the lag screw thread using molding technique. Optionally, the lag screw thread (comprising insert 570) is molded at a first stage, and the foil is applied at a second molding stage. Optionally, the foil comprises a rough internal surface (for example created by sand blasting) to provide a firm connection between the components. Alternatively and/or additionally, the foil is attached to the thread of the lag screw using mechanical means such as tiny pins. Additionally and/or alternatively, the foil is attached to the thread of the lag screw using adhesive means.

The above described embodiments and/or combinations of them may be incorporated to other bone screw types, and may be modified according to the need.

Figure 6:
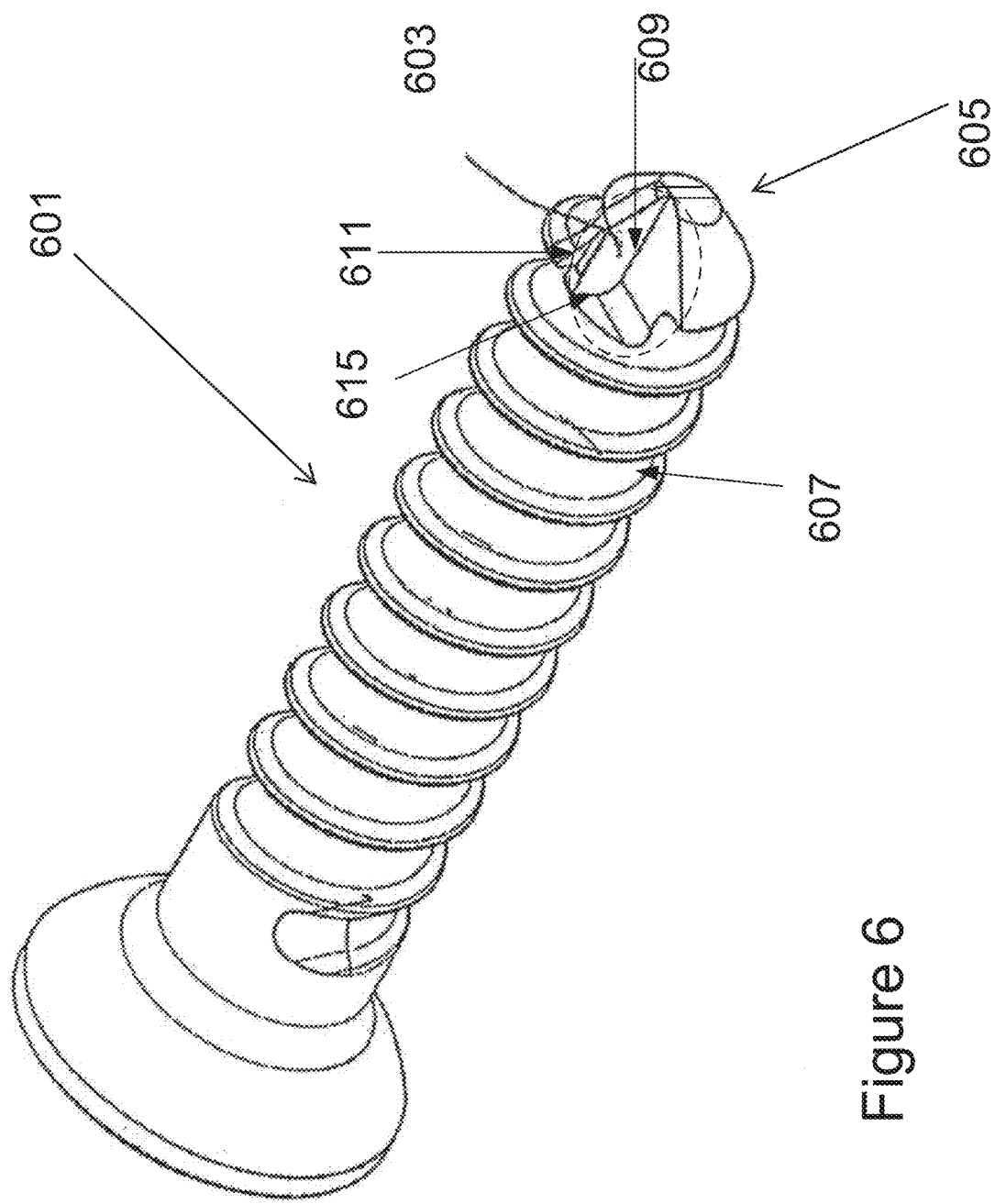
FIG. 6 is a drawing of a composite material bone screw comprising an embedded insert covering the edge of a cutting flute, according to an exemplary embodiment of this invention.

FIG. 6 illustrates an embodiment of a self tapping bone screw 601, comprising an insert 603. Optionally, screw 601 comprises a narrowing conical distal tip 605.

In some embodiments, as seen in this figure, tip 605 may include a cutting flute 615, extending, for example, between the end of thread 607 and the distal end of screw 601, along a portion of the conical tip 605.

In some embodiments, insert 603 covers at least a portion of cutting flute 615. In some embodiments, insert 603 may cover a portion such as portion 609 of a cutting flute, shaped to create a hole in the bone. Additionally or alternatively, insert 603 may cover a portion such as portion 611 of a cutting flute, extending between a first cutting tooth of thread 613 and distal end 605. Optionally, portion 611 is shaped to cut a thread as the screw is driven into the bone, for example expanding the cylindrical hole made by portion 609 of cutting flute.

Optionally, during manufacturing, the cutting flute is created by machining the distal tip 605 of screw 601. Alternatively, the cutting flute is created by molding screw 601 in a designated mold having the form of the cutting flute.

Figure 7:
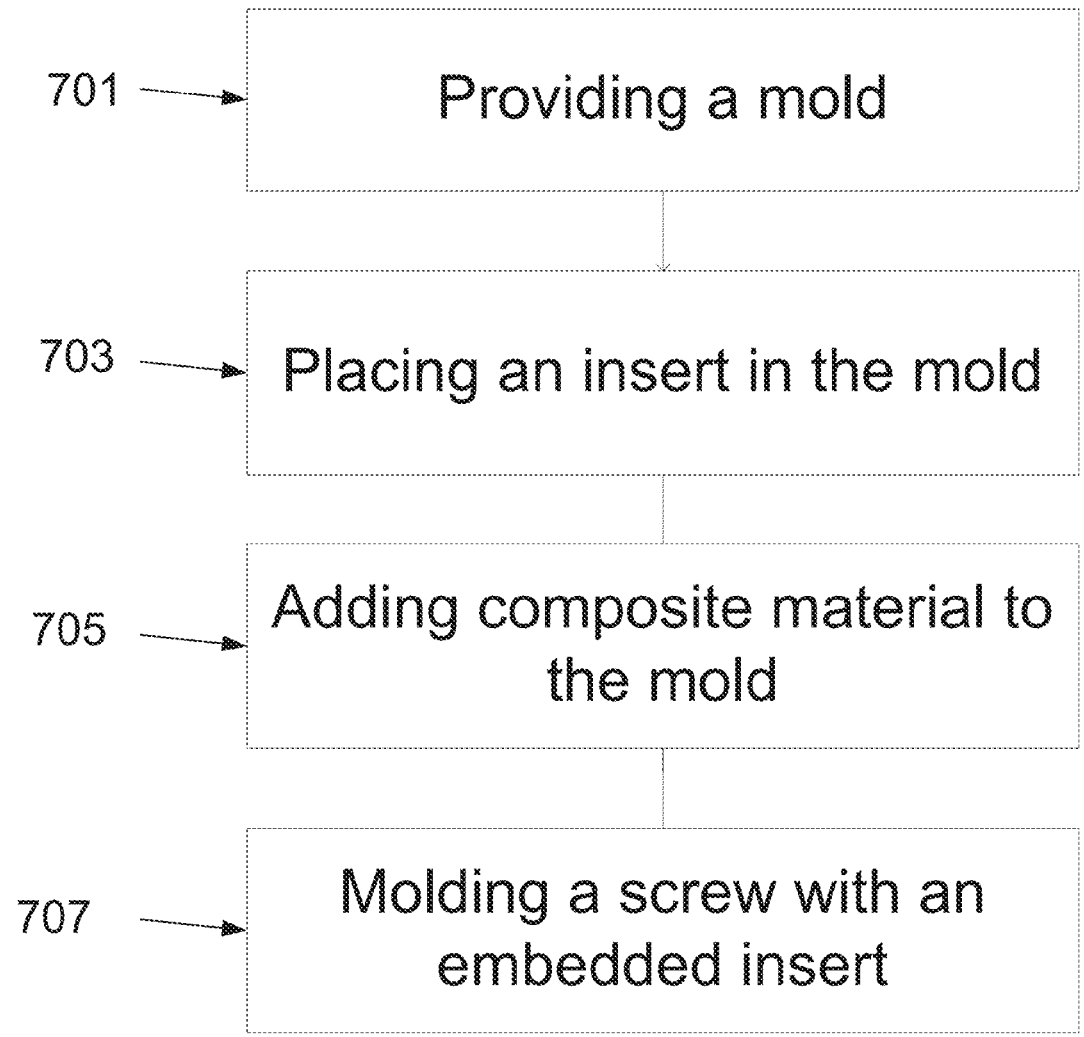
FIG. 7 is a flowchart of an exemplary molding method for embedding an insert within a composite material bone screw, according to some embodiments of this invention.

Manufacturing Methods of a Bone Screw with an Embedded Insert, According to Some Embodiments of the Invention FIG. 7 is a flowchart of an exemplary molding method for embedding an insert within a composite material bone screw, according to some embodiments of this invention.

As previously noted, the insert may be integrated to screw in various manners. For example, using adhesion means, and/or using a mechanical connection (such as small pins, optionally made of titanium), and/or using molding methods. The flowchart of FIG. 7 describes an exemplary molding method for manufacturing a screw with an embedded insert.

At 701, a mold, having at least along part of it a threaded (such as wave-like) configuration, is provided. Optionally, the mold comprises various shapes and/or sizes of screw rods and/or threads.

At 703, an insert is placed in the mold. Optionally, the insert is attached to the mold using, for example, a break-off piece. Optionally, the break off piece is removed from the insert at the end of the molding procedure, once the insert is embedded within the screw, as will be explained in the following figure.

At 705, composite material is added to the mold. Optionally, the composite material comprises prepreg tapes of fiber reinforced polymer, for example carbon fiber reinforced polymer PEEK or PEKK. Optionally, elongated forcing filaments of the composite material are arranged in the mold in a way that they surround at least a portion of the insert, for example the filaments are arranged above and below the insert. In some embodiments, the composite material, prior to molding, is formed in two or more portions, for example portions comprising multi layers of prepreg tape, or portions such as two halves of a rod (such as a rod cut longitudinally), and these portions are placed, for example, above and below the insert.

In some embodiments, the insert comprises holes, for example holes extending between two opposite faces of the insert, such that the composite material fills those holes upon molding, possibly strengthening the connection between the insert and screw. Optionally, elongated forcing filaments are passed through the holes of the insert.

At 707, the screw with the embedded insert is molded. Optionally, a compression molding process is used, and a press is used to axially press the composite material and force it to gain the shape of the mold, for example the shape of the thread at the mold circumference.

In some embodiments, compression molding is performed under conditions of high temperature and pressure, such as pressure higher than 100 Atm., optionally higher than 400 Atm., optionally higher than 700 Atm., optionally higher than 1,000 Atm.

In some embodiments, molding is performed to provide a rod with longitudinal fibers, and a thread with fibers that were forced into thread teeth. Optionally, the rod fiber elements at least at one of the rod ends are kept straight (tighten) out of the mold, optionally in a cold environment, while the circumference fiber elements are axially pressed, optionally by using a cylindrical shape press, so that they are forced to enter into the teeth-shape parts of the mold. Optionally, the orientation of fibers in the thread component complies with that of the thread pitch.

Additionally or alternatively, the longitudinal fiber elements of the rod as well as the circumference fiber elements are both axially pressed such that the longitudinal fiber elements of the rod are folded as well.

In some embodiments, the screw may be molded at a first stage, and the insert introduced at a second molding stage. Optionally, a slot may be fabricated and/or machined in the screw molding after the first molding stage, into which the insert is then introduced. A second molding stage is performed to embed the insert within the screw.

In some embodiments, using compression molding, a rod is produced with the embedded insert. The rod and insert are then machined together, to create the desired thread of the screw.

In some embodiments, the screw is molded, and then a slot is fabricated/and or machined in the screw. The insert may then be introduced to the slot and attached to the screw by adhesion means and/or mechanical connections, for example using small pins.

In some embodiments, any of the above described methods and/or combination of them may be used to manufacture a bone screw with an embedded insert.

Figure 8:
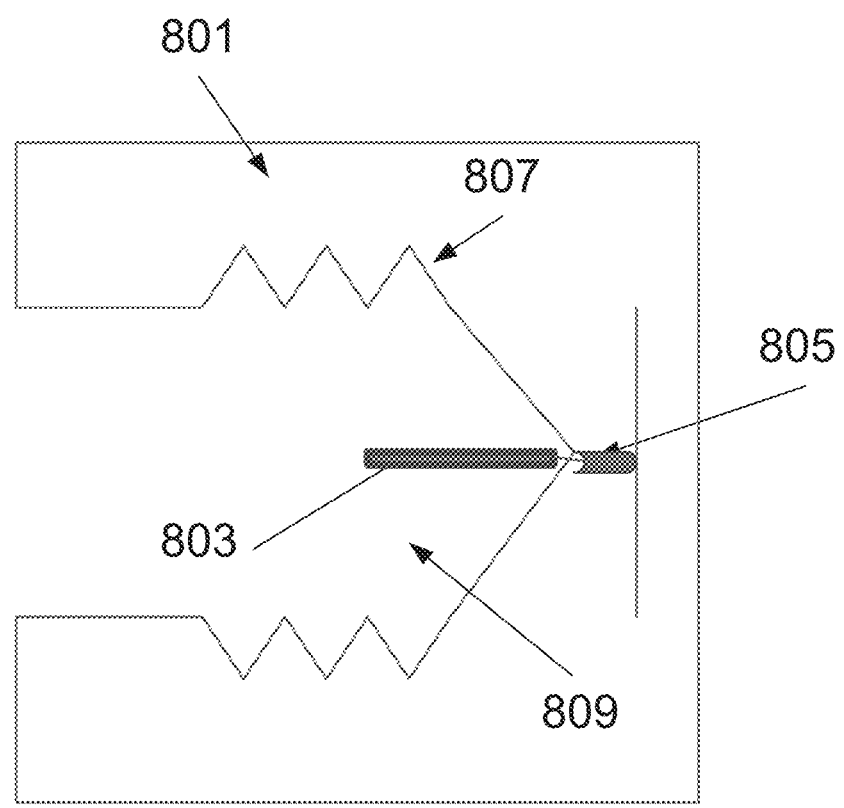
FIG. 8 is a schematic illustration of an exemplary mold for manufacturing a screw with an embedded insert, according to some embodiments of this invention.

FIG. 8 is a schematic illustration of an exemplary mold comprising an insert that was placed and/or attached to the mold, as explained in the previous figure. The mold may be used during manufacturing of a screw with an embedded insert using a compression molding process, according to an embodiment of this invention.

As shown in this figure, mold 801 comprises a wave-like configuration 807 for creating the designated shape of the screw thread.

In some embodiments, insert 803 is placed in a lumen 809 of mold 801 such that it is connected to the mold by a break-off piece 805. Optionally, break-off piece 805 is smaller than the insert. Optionally, break-off piece 805 is formed of the same material comprising insert 803, such as metal or ceramics. Optionally, break-off piece 805 has a thickness smaller than the thickness of insert 803, for example to allow its removal once the screw comprising embedded insert 803 is molded. In some embodiments, the break-off piece comprises a relatively wide portion on one end that is attached to the mold, and a narrow portion on the other end that is attached to the insert, and the latter may break easily once the screw and insert are molded together.

It is expected that during the life of a patent maturing from this application many relevant bone screws will be developed and the scope of the term bone screw is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A composite material bone screw comprising:
    a head configured at a proximal end of said screw;
    a body extending from said head to a distal end of said screw, said body at least partially threaded;
    an insert, said insert at least partially embedded within a distal portion of said body, wherein at least 60% of a total volume of said insert is enclosed within said composite material of said body, and wherein at least 60% of total surface area of said insert contacts said composite material of said body.

2. The insert according to claim 1, wherein a portion of said insert covers at least one cutting edge of said screw.

3. The insert according to claim 2, wherein said portion is an extension of said insert.

4. The insert according to claim 3, wherein said insert comprises a plurality of extensions for covering at least one cutting edge intended for self tapping.

5. The insert according to claim 3, wherein said extension is shaped according to a cross-section of a thread of said screw.

6. The insert according to claim 3, wherein said extension covers at least a perimeter of a cutting edge of said screw.

7. The insert according to claim 1, wherein said insert is sandwiched between two portions of said body.

8. The insert according to claim 1, wherein said insert is flat.

9. The insert according to claim 1, wherein said insert extends at least 3 mm along a long axis of the screw.

10. The insert according to claim 1, wherein said insert extends at least 2 mm along a diameter of the screw.

11. The insert according to claim 9, wherein said insert extends to the distal tip of said screw.

12. The screw according to claim 1, wherein said composite material comprises a fiber-reinforced polymer matrix.

13. The insert according to claim 1, wherein said insert is harder than a cortical bone.

14. The insert according to claim 1, wherein said insert is harder than said composite material of said body.

15. The screw according to claim 1, wherein at least one of said screw body and said insert comprises a radiopaque material thick enough for visualizing under fluoroscopy.

16. The insert according to claim 1, wherein said insert comprises holes extending between opposite faces of said insert.

17. The insert according to claim 16, wherein said holes are filled with a material of which said screw is made.

18. The screw according to claim 1, wherein said screw comprises a cutting flute.

19. The screw according to claim 1, wherein said screw is a lag screw.

20. The screw according to claim 1, wherein a thin hard foil covers at least 70% of a thread of said screw, and does not cover said insert.

21. The screw according to claim 1, wherein said insert is embedded within said distal portion of said body such that most of said insert does not extend axially past said distal end of said composite material body.

* * * * *